US011560557B2

(12) United States Patent
Friend et al.

(10) Patent No.: US 11,560,557 B2
(45) Date of Patent: Jan. 24, 2023

(54) ACOUSTIC WAVE BASED PARTICLE AGGLOMERATION

(71) Applicants: The Regents of the University of California, Oakland, CA (US); James Friend, San Diego, CA (US); Kenjiro Takemura, Yokohama (JP); Yuta Kurashina, Yokohama (JP)

(72) Inventors: James Friend, San Diego, CA (US); Kenjiro Takemura, Yokohama (JP); Yuta Kurashina, Yokohama (JP)

(73) Assignee: The Regents of the University of California, Oakland, CA (US)

( * ) Notice: Subject to any disclaimer, the term of this patent is extended or adjusted under 35 U.S.C. 154(b) by 273 days.

(21) Appl. No.: 16/461,753

(22) PCT Filed: Nov. 17, 2017

(86) PCT No.: PCT/US2017/062256
§ 371 (c)(1),
(2) Date: May 16, 2019

(87) PCT Pub. No.: WO2018/094189
PCT Pub. Date: May 24, 2018

(65) Prior Publication Data
US 2019/0359968 A1 Nov. 28, 2019

Related U.S. Application Data

(60) Provisional application No. 62/242,098, filed on Nov. 18, 2016.

(51) Int. Cl.
*C12N 13/00* (2006.01)
*B01L 3/00* (2006.01)
(Continued)

(52) U.S. Cl.
CPC ............ *C12N 13/00* (2013.01); *B06B 1/0215* (2013.01); *B06B 1/06* (2013.01); *B06B 1/0603* (2013.01);
(Continued)

(58) Field of Classification Search
CPC ...................................................... C12M 47/02
See application file for complete search history.

(56) References Cited

U.S. PATENT DOCUMENTS 5,085,783 A    2/1992  Feke et al.
5,164,094 A  * 11/1992  Stuckart .................... C02F 1/52
                                                        210/708
(Continued)

OTHER PUBLICATIONS

Alvarez, M. et al., "Surface Vibration Induced Spatial Ordering of Periodic Polymer Patterns on a Substrate." Langmuir, 2008, 24, 10629-10632.
(Continued)

*Primary Examiner* — Nathan A Bowers
(74) *Attorney, Agent, or Firm* — Mintz Levin Cohn Ferris Glovsky and Popeo, P.C.

(57) ABSTRACT

Articles of manufacture, including an apparatus for acoustic wave based agglomeration, are provided. The apparatus may include a well and an acoustic wave device. The well may be configured to hold a suspension that includes a plurality of particles. The acoustic wave device may be configured to generate a plurality of acoustic waves. The plurality of acoustic waves inducing acoustic streaming within the suspension. The acoustic streaming agitating the suspension to form an agglomerate comprising at least a portion of the plurality of particles. Methods for acoustic wave based agglomeration are also provided.

15 Claims, 18 Drawing Sheets

(51) Int. Cl.
| | |
|---|---|
| *B06B 1/02* | (2006.01) |
| *B06B 1/06* | (2006.01) |
| *C12M 1/00* | (2006.01) |
| *C12M 1/26* | (2006.01) |
| *C12M 3/00* | (2006.01) |
| *G01N 1/40* | (2006.01) |

(52) U.S. Cl.
CPC .............. *C12M 3/00* (2013.01); *C12M 33/08* (2013.01); *C12M 47/02* (2013.01); *B01L 2200/0647* (2013.01); *B06B 2201/77* (2013.01); *G01N 2001/4094* (2013.01)

(56) References Cited

U.S. PATENT DOCUMENTS

| | | | |
|---|---|---|---|
| 7,942,568 | B1 | 5/2011 | Branch et al. |
| 2004/0124155 | A1* | 7/2004 | Meegan, Jr. ......... B01D 53/565 95/29 |
| 2005/0074477 | A1 | 4/2005 | Josimovic-Alasevic et al. |
| 2005/0271559 | A1* | 12/2005 | Ratcliff .............. B01D 39/2068 422/128 |
| 2013/0000420 | A1* | 1/2013 | Manneberg .......... B01J 19/0046 73/863 |
| 2013/0330247 | A1 | 12/2013 | Wilson et al. |
| 2014/0011240 | A1* | 1/2014 | Lipkens ................ H01L 41/053 435/71.1 |
| 2016/0129370 | A1 | 5/2016 | Lipkens et al. |
| 2016/0186126 | A1* | 6/2016 | Laugharn, Jr. ......... C12M 45/02 435/306.1 |
| 2016/0319270 | A1* | 11/2016 | Lipkens .............. A61M 1/3678 |
| 2016/0363579 | A1* | 12/2016 | Gilmanshin ...... B01L 3/502761 |
| 2018/0369815 | A1* | 12/2018 | Zheng .............. B01L 3/502761 |
| 2021/0123038 | A1* | 4/2021 | Musiak ................. B06B 1/0261 |

OTHER PUBLICATIONS

Bernassau, A. L. et al., "Two-dimenstional manupulation of micro particles by acoustic radiation pressure in a heptagon cell." IEEE Trans. Ultrason., Ferroelect., Freq. Contr., 2011, 58, 2132-2138.
Blamey, J. et al., "Microscale Capillary Wave turbulence Excited by High Frequency Vibration." Langmuir, 2013, 29, 3835-3845.
Bok, M. et al., "The Dynamics of Surface Acoustic Wave-Driven Scaffold Cell Seeding." Biotechnol. Bioeng., 2009, 103, 387-401.
Darbre, P. et al., "Effect of Estradiol on Human Breast Cancer Cells in Culture." Cancer Res., 1983, 43, 349-354.
Ding, X. et al., "Standing surface acoustic wave (SSAW) based multichannel cell sorting." Lab Chip, 2012, 12, 4228-4231.
Freshney, R. I., Culture of Animal Cells: A Manual of Basic Technique and Specialized Applications, Wiley-Blackwell, New Jersey, 6th edn, 2010.
Frey, O. et al., "Reconfigurable microfluidic hanging drop network for multi-tissue interaction and analysis." Nat. Commun., 2014, 5:4250, 1-11.
Gesellchen, F. et al., "Cell patterning with a heptagon acoustic tweezer-application in neurite guidance." Lab Chip, 2014, 14, 2266-2275.
Hegde, M. et al., Dynamic Interplay of Flow and Collagen Stabilizes Primary Hepatocytes Culture in a Microfluidic Platform. Lab Chip, 2014, 14, 2033-2039.
Hintzsche, H. et al., Hyperthermia-induced micronucleus formation in a human keratinocyte cell line. Mutat Res. Oct.-Nov. 2012, 738-739:71-4.
Hodgson, R.P. et al., "Transmitting high power rf acoustic radiation via fluid couplants into superstrates for micofluidic." Appl. Phys. Lett., 2009, 94, 024102.
Hoyos, M. et al., "Controlling the acoustic streaming by pulsed ultrasounds." Ultrasonics, Jan. 2013, vol. 53:1, pp. 70-76.
Hultstroem, J. et al., "Proliferation and viability of adherent cells manipulated by standing-wave ultrasound in a microfluidic chip." Ultrasound Med. Biol., Jan. 2007, 33:1, pp. 145-151.

Kujawska, T. et al., "Impact of thermal effects induced by ultrasound on viability of rate C6 glioma cells." Ultrasonics, 2014, 54, 1366-1372.
LaBarbera, D. V. et al., "The multicellular tumor spheroid model for high-throughput cancer drug discovery." Expert Opin. Drug Discov., Sep. 2012, 7:9, 819-830.
Lee, J. et al., "Microfluidic acoustic trapping force and stiffness measurement using viscous drag effect." Ultrasonics, Jan. 2013, 53:1, 249-254.
Li, H. et al., "Microfluidic Colloidal Island Formation and Erasure Inducted by Surface Acoustic Wave Radiation." Phys. Rev. Lett., 2008, 101, 084502.
Li, H. et al., "Surface acoustic wave concentration of particle and bioparticle suspensions." Biomed. Microdevices, 2007, 9, 647-656.
Lin, R.-Z. et al., "Recent advances in three-dimensional multicellular spheriod culture for biomedical research." Biotechnol. J., 2008, 3, 1172-1184.
Lovitt, C. J. et al., "Advanced Cell Culture Techniques for Cancer Drug Discovery." Biology, 2014, 3, 345-367.
Manneberg, O. et al., "Wedge transducer design for two-dimensional ultrasonic manipulation in a nicrofluidicchip." 2008, J. Micromech. Microeng. 18, 095025.
Mayol, L. et al., "Design of electrospayed non-spherical poly (L-lactide-co-glicolide) microdevices for sustained drug delivery." J. Mater. Sci.: Mater. Med., 2014, 25, 383-390.
Mehta, G. et al., "Opportunities and challenges for use of Tumor Spheroids as Models to Test Drug Delievery and Efficacy." J. Control Release, 2012, 164(2), 192-204.
Napolitano, A. P. et al., Dynamics of Self-Assembly of Complex Aggregates on Micromolded Nonadhesive Hydrogels. Tissue Eng., 2007, 13, 2087-2094.
Nyberg, S. L. et al., "Rapid, Large-Scale Formation of Porcine Hepatocyte Spheroids in a Novel Spheroid Reservoir Bioartificial Liver." Liver Transpl., 2005, 11, 901-910.
Richter, C. et al., "Spatially controlled cell adhesion on three-dimensional substrates." Biomed. Microdevices, 2010, 12, 787-795.
Rogers, P. R. et al., "Explotation of surface acoustic waves to drive size-dependent microparticle concentration within a droplet." Lab Chip, 2010, 10, 2979-2985.
Seah, S. A. et al., "Correspondence: Dexterous ultrasonic levitation of millimeter-sized objects in air." IEEE Trans. Ultrason., Ferroelect., Freq. Contr., 2014, 61, 1233-1236.
Shi, X. et al., "Quantitative investigation of acoustic streaming in blood." J. Acoust. Soc. Am., 2002, 111(2), 1110-1121.
Shilton, R. et al., "Particle concentration and mixing in microdrops driven by focused surface acoustic waves." J. Appl. Phys., 2008, 104, 014910.
Shilton, R. J. Sens. "Quantification of surface acoustic wave induced chaotic mixing-flows in microfluidic wells." Sensors and Actuator B: Chem., 2011, 160, 1565-1572.
Song, H. et al., "Spatial Composition of Prostate Cancer Spheroids in Meixed and Static Cultures." Tissue Eng., 2004, 10, 1266-1276.
Song, A. S. et al., "Thermally Induced Apoptosis, Necrosis, and Heat shock Protein Expression in Three-dimensional Culture." J. Biomech. Eng., 2014, 136(7), 071006.
Speit, G. et al., "Hyperthermia-induced genotoxic effects of human A549 cells." Mutation Ressearch/Fundamental and Molecular Mechanisms of Mutagenesis, 2013, vols. 747-748, 1-5.
Sutherland, R. M., "Cell and environment interaction in tumor microregions: the multicell spheroid model." Science, Apr. 8, 1988, vol. 240, Issue 4849. pp. 177-184.
Tibbitt, M. W. et al., "Hydrogels as Extracellular Matrix Mimics for 3D Cell Culture." Biotechnol. & Bioeng., 2009, vol. 103, No. 4, 655-663.
Tripathi, S. et al., "Performance study of microfluidic devices for blood plasma separation—a designer's perspective." J. Micromech. & Microeng., 2015, 25, 084004.
Vanherberghen, B. et al., "Ultrasound-controlled cell aggregation in a multi-well chip." Lab Chip, 2010, 10, 2727-2732.

(56) References Cited

OTHER PUBLICATIONS

Zhou, M. et al., "Induction of epithelial-to-mesenchymal transition in proximal tubular epithelial cells on microfluidic devices." Biomaterials, 2014, vol. 35, 1390-1401.

* cited by examiner

ACOUSTIC WAVE BASED PARTICLE AGGLOMERATION

RELATED APPLICATION

This application is a national phase entry of Patent Cooperation Treaty Application PCT/US2017/062256 filed Nov. 17, 2017, entitled "ACOUSTIC WAVE BASED PARTICLE AGGLOMERATION," which claims priority to U.S. Provisional Patent Application No. 62/424,098 file on Nov. 18, 2016 and entitled SPHEROID FABRICATION IN WELL TRAYS USING ULTRASOUND, the disclosure of which is incorporated herein by reference in its entirety.

TECHNICAL FIELD

The subject matter described herein relates generally to tissue engineering and more specifically to techniques for forming cell agglomerates.

BACKGROUND

A cell agglomerate may refer to a three-dimensional cell formation such as, for example, a spheroid of cells. Cell agglomerates may provide a more realistic representation of an in vivo environment than two-dimensional cell formations such as, for example, a monolayer of cells. As such, cell agglomerates may have a variety of clinical and research applications. For example, cancerous cell agglomerates that replicate tumors may be used in the development of treatments such as, for instance, chemotherapy, radiation therapy, and/or the like. In doing so, these cell agglomerates may provide an exemplary in vitro supplement and/or alternative to animal testing.

SUMMARY

Articles of manufacture, including apparatuses, and methods for acoustic wave based agglomeration are provided. An apparatus for acoustic wave based agglomeration may include a well and an acoustic wave device. The well may hold a suspension that includes a plurality of particles. The acoustic wave device may be configured to generate a plurality of acoustic waves. The plurality of acoustic waves may induce acoustic streaming within the suspension. The acoustic streaming may agitate the suspension to form an agglomerate comprising at least a portion of the plurality of particles.

In some variations, one or more features disclosed herein including the following features can optionally be included in any feasible combination. The agglomerate may be a 3-dimensional formation that includes at least the portion of the plurality of particles. The plurality of particles may be cells. The suspension may be a mixture of the plurality of particles and one or more fluids.

In some variations, the acoustic wave device may include a piezoelectric material configured to convert electric energy into the plurality of acoustic waves. The piezoelectric material may include a monocrystalline and/or a polycrystalline. In order to cause the acoustic wave device to generate the plurality of acoustic waves, between 50 milliwatts to 5.0 watts of electric power may be applied to the acoustic wave device.

In some variations, the acoustic wave device may be configured to generate the plurality of acoustic waves in one or more intermittent bursts. A length of the one or more intermittent bursts of acoustic waves may be between 1 second and 100 seconds. Each of the one or more intermittent bursts of acoustic waves may trigger a corresponding cycle of the acoustic streaming. The acoustic wave device may be configured to expose the suspension to between 1 cycle and 1000 cycles of the acoustic streaming. Each cycle of the acoustic streaming may be between 0.1 seconds per minute to 15 seconds per minute In some variations, the acoustic wave device may be configured to operate in accordance with a duty ratio. The duty ratio may correspond to a proportion of total elapsed time during which the acoustic wave device is generating the plurality of acoustic waves. The duty ratio may be between 10% and 50%.

In some variations, the apparatus may further include a couplant material configured to transmit the plurality of acoustic waves from the acoustic wave device to the well. The acoustic wave device may be oriented such that the plurality of acoustic waves enters a bottom of the well at between an 5° angle of incidence and an 55° angle of incidence. The acoustic wave device may be oriented such that the acoustic streaming is induced at between ½ to ¾ of a distance between from a center of the well and an edge of the well.

A method for acoustic wave based agglomeration includes generating, by an acoustic wave device, a plurality of acoustic waves. The plurality of acoustic waves may induce acoustic streaming within a suspension comprising a plurality of particles. The suspension may be held in a well. The acoustic streaming may agitate the suspension to form an agglomerate that includes at least a portion of the plurality of particles In some variations, one or more features disclosed herein including the following features can optionally be included in any feasible combination. The agglomerate may be a 3-dimensional formation that includes at least the portion of the plurality of particles. The plurality of particles may be cells. The suspension may be a mixture of the plurality of particles and one or more fluids.

In some variations, a piezoelectric material included in the acoustic wave device may convert electric energy into the plurality of acoustic waves. In order to cause the acoustic wave device to generate the plurality of acoustic waves, between 50 milliwatts and 3.0 watts of power may be applied to the piezoelectric material.

In some variations, the acoustic wave device may generate the plurality of acoustic waves in one or more intermittent bursts. A length of the one or more intermittent bursts of acoustic waves is between 1 second and 100 seconds. Each of the one or more intermittent bursts of acoustic waves may trigger a corresponding cycle of acoustic streaming. The acoustic wave device may expose the suspension to between 1 cycle and 1000 cycles of the acoustic streaming. Each cycle of the acoustic streaming may be between 0.1 seconds per minute to 15 seconds per minute.

In some variations, the acoustic wave device may be operated in accordance with a duty ratio corresponding to a proportion of total elapsed time during which the acoustic wave device is generating the plurality of acoustic waves. The duty ratio may be between 10% and 50%.

In some variations, the plurality of acoustic waves may be transmitted from the acoustic wave device to the well via a couplant material. The acoustic wave device may be oriented such that the plurality of acoustic waves enters a bottom of the well at between an 5° angle of incidence and an 55° angle of incidence. The acoustic wave device may be oriented such that the acoustic streaming is induced at between ½ to ¾ of a distance between a center of the well and an edge of the well.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a rechargeable battery, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, and/or elements.

DETAILED DESCRIPTION

Despite the many clinical and research applications for cell agglomerates, conventional techniques for forming cell agglomerates may not be viable for high volume production of quality cell agglomerates. For instance, cell agglomerates may be formed by stirring a cell culture with a spinner flask, but the resulting cell agglomerates may be inconsistent in size. Other techniques for forming cell agglomerates such as, for example, micromolding and hanging-drop, may yield cell agglomerates that are uniform in size. However, these agglomeration techniques may be cost prohibitive due to technical complexities such as, for example, the requirement for agarose gels cast from three-dimensional printed micromolds, microarrays made via photopolymerization, and/or micropatterns generated on an inverted polydimethyl-siloxane substrate. As such, in some example embodiments, cell agglomerates may be formed by at least exposing cells to ultrasonic energy such as, for example, acoustic waves and/or the like.

In some example embodiments, an apparatus for acoustic wave based agglomeration may include one or more wells for holding a suspension, which may be a heterogeneous mixture that includes a fluid and a plurality of solid particles such as cells. The apparatus for acoustic wave based agglomeration may further include an acoustic wave device configured to generate a plurality of acoustic waves. The acoustic wave device may include a piezoelectric material such as, for example, a monocrystalline (e.g., lithium niobate, quartz, lithium tantalate, langasite, and/or the like), a polycrystalline (e.g., ceramic and/or the like), and/or the like. As such, the acoustic wave device may generate the plurality of acoustic waves as a response to being subject to an electric field. The plurality of acoustic waves generated by the acoustic wave device may be delivered to the one or more wells via a couplant material configured to enable the transmission of ultrasonic energy such as, for example, acoustic waves and/or the like. The plurality of acoustic waves may generate, within each of the one or more wells, a vortex that causes the suspended particles (e.g., cells) to form agglomerations such as, for example, spheroids and/or the like. It should be appreciated that the use of acoustic waves may produce uniformly sized cell agglomerations that are substantially (e.g., 15 times) larger than cell agglomerations formed using conventional agglomeration techniques. These larger cell agglomerations may be more viable test specimen than the smaller cell agglomerations generated using conventional agglomeration techniques.

Figure 1A:
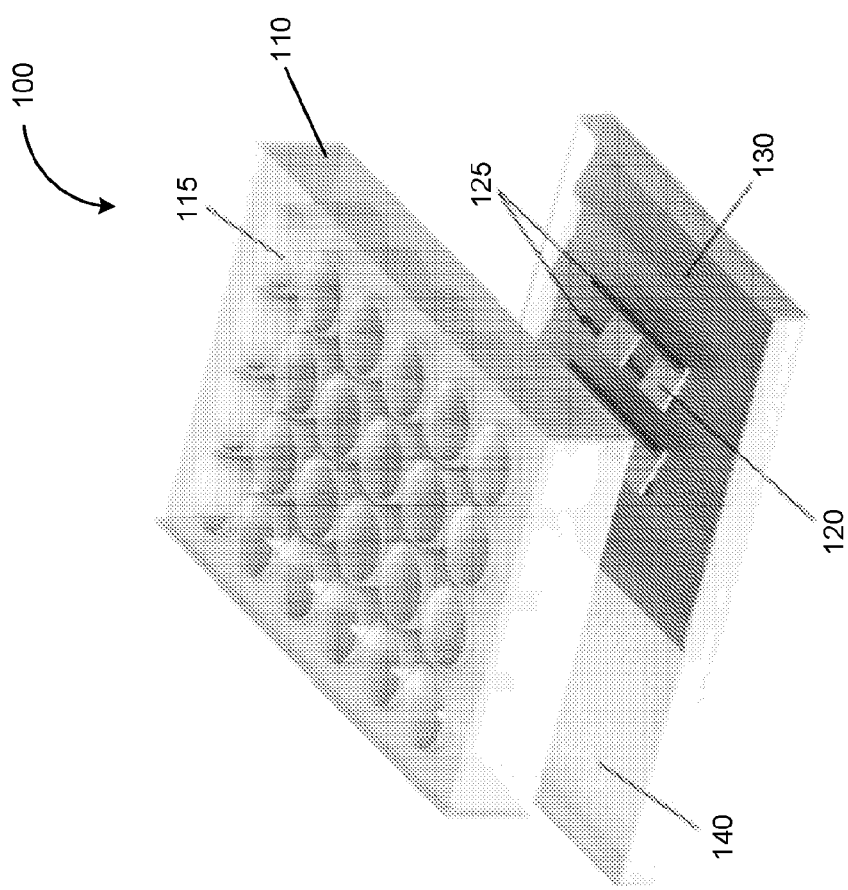
FIG. 1A depicts a perspective view of an apparatus for acoustic wave based agglomeration, in accordance with some example embodiments.
Figure 1B:
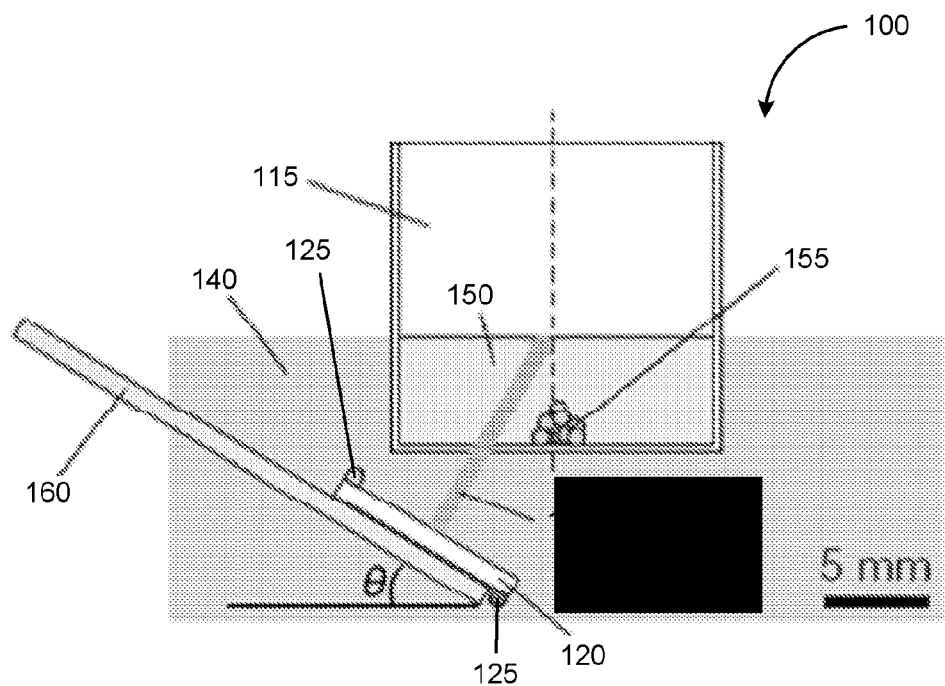
FIG. 1B depicts a side view of an apparatus for acoustic wave based agglomeration, in accordance with some example embodiments.
Figure 1C:
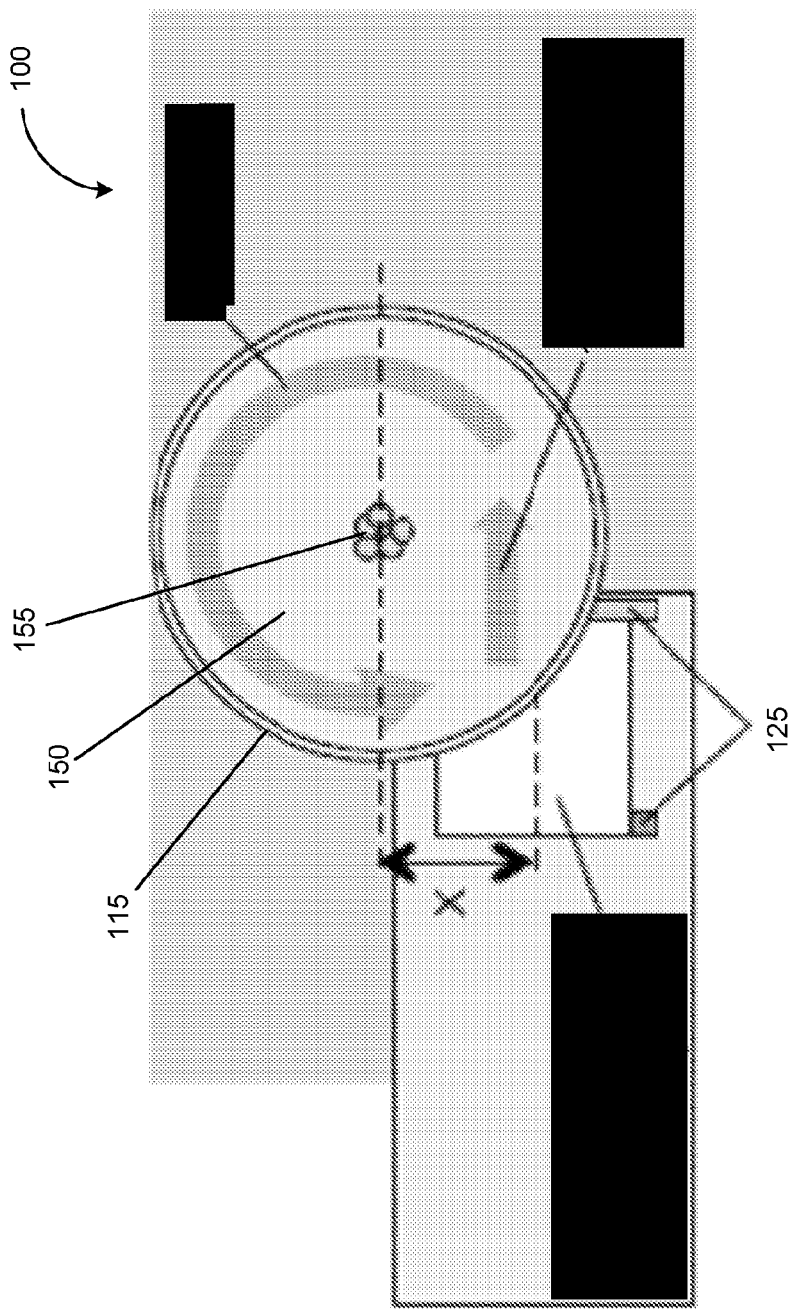
FIG. 1C depicts a top view of an apparatus for acoustic wave based agglomeration, in accordance with some example embodiments.

FIGS. 1A-C depict an apparatus 100 for acoustic wave based agglomeration, in accordance with some example embodiments. Referring to FIGS. 1A-C, the apparatus 100 may include an acoustic wave device 120. The apparatus 100 may further include one or more wells including, for example, a well 115. The well 115 may be configured to hold a suspension 150, which may be a heterogeneous mixture that includes a plurality of solid particles. For instance, the solid particles may be a biological material such as cells and/or a nonbiological material. It should be appreciated that the well 115 may be any type of receptacle, container, and/or reservoir. Furthermore, as shown in FIG. 1A, the well 115 may be part of a well plate 110 that includes a plurality of individual wells. Here, it should be appreciated that the well plate 110 may include any number of wells including, for example, 24 wells, 48 wells, and/or the like. The well plate 110 including the well 115 may be coupled with a couplant material 140. For instance, the well plate 110 including the well 115 may be in contact with the couplant material 140 and/or at least partially submerged within the couplant material 140.

In some example embodiments, the acoustic wave device 120 may include a piezoelectric material such as, for example, a monocrystalline (e.g., lithium niobate, quartz, lithium tantalate, langasite, and/or the like), a polycrystalline (e.g., ceramic and/or the like). For instance, as shown in FIGS. 1A-C, the acoustic wave device 120 may include one or more monocrystalline and/or polycrystalline plates. The acoustic wave device 120 may be configured to operate at 2.134 megahertz (or a different frequency) in order to optimize the formation of an agglomerate 155 within the well 115. As shown in FIGS. 1A-C, the acoustic wave device 120 may include wiring 125, which may supply an electric current to the piezoelectric material included in the acoustic wave device 120. The acoustic wave device 120 may generate a plurality of acoustic waves 160 when the piezoelectric material included in the acoustic wave device 120 converts electric energy into mechanical energy in the form of acoustic waves such as, for example, surface acoustic waves, Lamb waves, flexural waves, thickness mode vibrations, mixed-mode waves, longitudinal waves, shear mode vibrations, bulk wave vibrations, and/or the like.

According to some example embodiments, the acoustic waves 160 may be burst waves generated using pulse width modulation (PWM). As such, the suspension 150 in the well 115 may be subject to intermittent acoustic waves instead of constant acoustic waves. In order to generate burst waves, the power that is input into the acoustic wave device 110 (e.g., via the wiring 125) may alternate between zero and a constant amplitude level. The use of burst waves may reduce overall power and the concomitant risk of overheating the suspension 150. For instance, when the suspension 150 is subject to intermittent acoustic waves over a period of 10 minutes, the temperature of the suspension 150 remained between 23° C. and 26° C. As the agglomerate 155 may be formed from living cells, maintaining the temperature of the suspension 150 may be critical for preserving the viability of the agglomerate 155. High temperatures (e.g., in excess of 40° C.) may cause cellular death.

The acoustic waves 160 may be delivered to the well 150 via the couplant material 140. As noted, the couplant material 140 may be configured to enable the transmission of ultrasonic energy such as, for example, the acoustic waves 160 generated by the acoustic wave device 110. According to some example embodiments, the couplant material 140 may include water and glycerol, although the couplant material 140 may have a different composition.

The acoustic waves 160 generated by the acoustic device 110 may induce acoustic streaming 162 in the suspension 150. The acoustic streaming 162 may be the non-laminar and/or turbulent fluid flow that result from variations in a density of the suspension 150 and variations in a velocity of the suspension 150 due to agitation from the acoustic waves 160 generated by the acoustic wave device 110. As shown in FIG. 1C, the acoustic streaming 162 may cause the formation of a vortex 164 within the suspension 150. It should be appreciated that the vortex 164 may be a region in the suspension 150 in which the suspension 150 revolves around a straight axis and/or a curved axis. The vortex 164 may cause the particles (e.g., cells) in the suspension 150 to agglomerate, thereby forming the agglomerate 155. For instance, the vortex 164 may cause a shear-induced migration of the solid particles in the suspension 150, which may concentrate at least a portion of these solid particles toward a center of the well 115. The agglomerate 155 may be a three-dimensional formation of the solid particles included in the suspension 150. For example, the agglomerate 155 may be a spheroid of cells and/or the like.

In some example embodiments, the apparatus 100 may include one or more mechanisms for orienting the acoustic wave device 120 relative to the well 115. As shown in FIG. 1A, the acoustic wave device 120 may be deposed on a base plate 130 configured to maintain the orientation of the acoustic wave device 120 relative to a base of the well 115. The base plate 130 may be formed from any suitable material including metals such as, for example, aluminum (Al) and/or the like. Moreover, the base plate 130 may be fabricated to include and/or support one or more staggered ramps including, for example, a ramp 160. The one or more ramps (e.g., the ramp 160) may be formed from any suitable material including, for example, glass and/or the like.

The orientation of the acoustic device 120 relative to the well 115 may determine the angle of incidence θ at which the acoustic waves 160 enters the well 115 and into the suspension 150. For instance, as shown in FIG. 1C, the one or more staggered ramps (e.g., the ramp 160) may position the acoustic wave device 120 (e.g., the monocrystalline and/or polycrystalline plates) at an angle θ (e.g., θ=20°) with respect to the base of the well 115. The angle θ may correspond to the angle of incidence θ at which the acoustic waves 160 enters the well 115 and into the suspension 150. Alternatively and/or additionally, the orientation of the acoustic device 120 relative to the well 115 may also determine the radial location x of the acoustic streaming 162. As shown in FIG. 1C, the radial location x may corresponding a distance between the acoustic streaming 162 in the suspension 150 and a center of the well 115.

In some example embodiments, the formation of the agglomerate 155 may depend on a number of parameters including, for example, the angle of incidence θ and/or the radial location x. Alternatively and/or additionally, the formation of the agglomerate 155 may also depend on an input power E applied to the acoustic wave device 110, a duty ratio D of the acoustic waves 160, a total exposure time $T_d$ to the acoustic waves 160, a length of a burst period $T_b$ of the acoustic waves 160, a concentration $N_p$ of the solid particles within the suspension 150, and/or a length of each exposure cycle $T_i$ to the acoustic streaming 162. Table 1 below summarizes these parameters. It should be appreciated that these parameters may affect the formation of the agglomerate 155 including, for example, a size of the agglomerate 155, a location of the agglomerate 155 within the well 115, and/or a location of unagglomerated solid particles within the well 115.

TABLE 1

| Conditions | Parameters |
| --- | --- |
| Angle of ultrasound incident into the fluid, θ (deg.) | 0, 5, 10, 15, 20, 25, 30, 35, 40, and 45 |
| Radial location of the ultrasound, x (mm) | 0, 2.5, 5.0, and 7.5 |
| Input electric power, E (W) | 1.0, 1.5, 2.0, and 3.0 |
| On-off duty ratio of the ultrasound, D (%; 100% = continuously on) | 25, 50, 75, and 100 |

TABLE 1-continued

| Conditions | Parameters |
| --- | --- |
| Total time of exposure, $T_d$ (s) | 30 |
| Acoustic streaming exposure burst time period, $T_b$ (ms) | 2, 12, 16, 20, 24, and 200 |
| Number of particles in the fluid sample, $N (\times 10^6)$ | 0.01, 0.05, 0.1, 1, and 5 |

FIGS. 2A-E depicts a relationship between the angle of incidence θ and the formation of the agglomerate 155, in accordance with some example embodiments. Referring to FIGS. 1A-C and 2A-E, the formation of the agglomerate 155 may be affected by varying the angle of incidence θ, for example, over a range between 0° and 45° (e.g., 0°<θ<45°). As shown in FIGS. 2A-E, the formation of agglomerate 155 may vary at different angles of incidence including, for example, 20°, 25°, and 30°, while the other parameters are held constant. For example, the radial location x may be fixed at 5.0 millimeters, the input power E may be fixed at 3.0 watts, the duty ratio D may be fixed at 100%, the total exposure time $T_d$ may be fixed to 30 seconds, and the concentration $N_p$ may be fixed to $1.0 \times 10^4$ particles per milliliter.

Figure 2A:
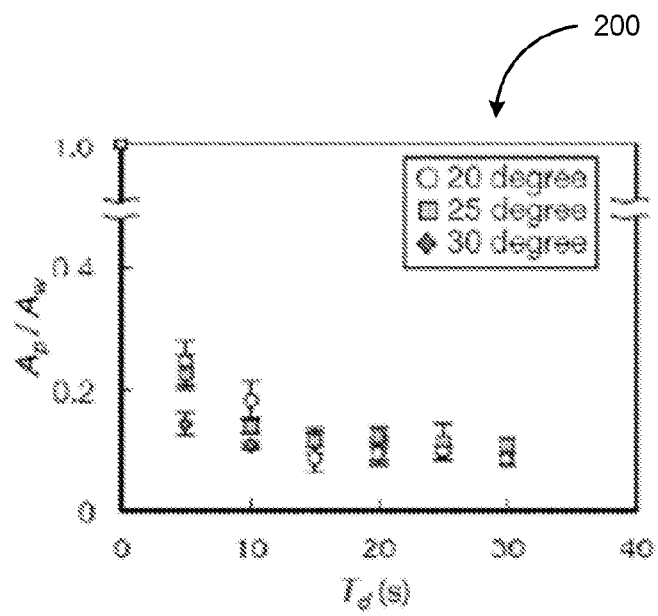
FIG. 2A depicts a graph illustrating agglomerate formation at different angles of incidence, in accordance to some example embodiments.
Figure 2B:
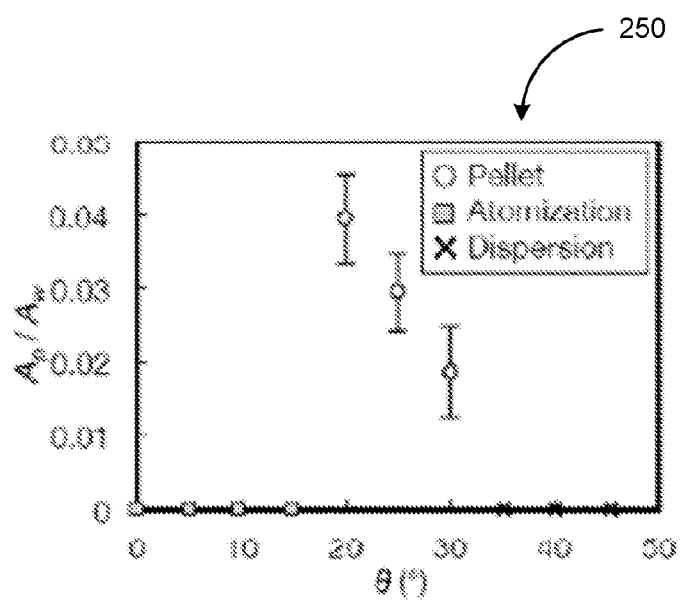
FIG. 2B depicts a graph illustrating agglomerate formation at different angles of incidence, in accordance to some example embodiments.

To further illustrate, FIGS. 2A-B depict graphs illustrating the formation of the agglomerate 155 at different angles of incidence θ, in accordance with some example embodiments. Referring to FIGS. 2A-B, the formation of the agglomerate 155 may be quantified based on a ratio $$\frac{A_p}{A_w},$$

wherein $A_p$ may correspond to a cross-sectional area occupied by the agglomerate 155 and $A_w$ may correspond to a cross-sectional area of the well 115. FIG. 2A depicts a graph 200 illustrating a change in the ratio $$\frac{A_p}{A_w}$$

at different angles of incidence θ (e.g., 20°, 25°, and 30°) over the duration of the total exposure time $T_d$.

$$\frac{A_p}{A_w}$$

Figure 2C:
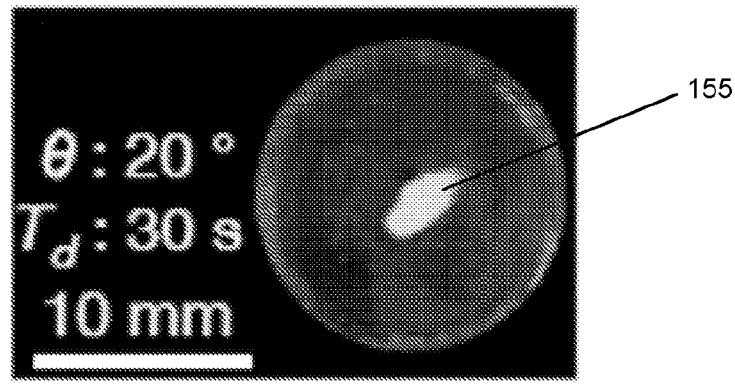
FIG. 2C depicts an image of an agglomerate formed at a 20° angle of incidence, in accordance with some example embodiments.
Figure 2D:
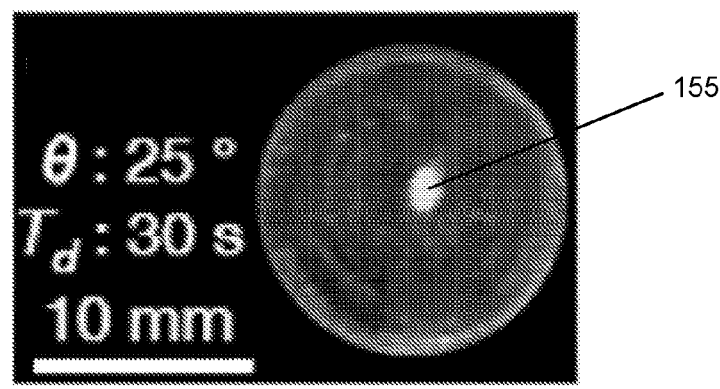
FIG. 2D depicts an image of an agglomerate formed at a 25° angle of incidence, in accordance with some example embodiments.
Figure 2E:
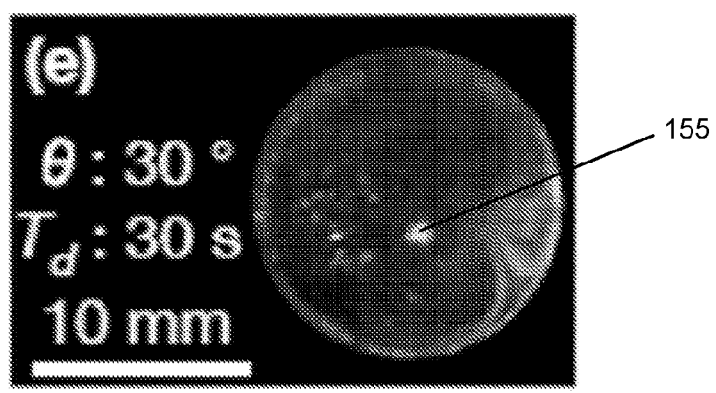
FIG. 2E depicts an image of an agglomerate formed at a 30° angle of incidence, in accordance with some example embodiments.

Meanwhile, FIG. 2B depicts a graph 250 illustrating the relationship between me ratio and the angle of incidence θ. FIGS. 2C-E depict images of the agglomerate 155 formed at different angles of incidence θ including, for example, 20°, 25°, and 30°. For example, FIG. 2C depicts an image of the agglomerate 155 formed at an 20° angle of incidence, FIG. 2D depicts an image of the agglomerate 155 formed at an 25° angle of incidence, and FIG. 2E depicts an image of the agglomerate 155 formed at an 30° angle of incidence.

The formation of the agglomerate 155 may be optimized when the angle of incidence θ maximizes a portion of the acoustic waves 160 entering the well 115 and/or minimizes a portion of the acoustic waves 160 that fails to enter the well 115. As shown in FIGS. 2A-E, the formation of the agglomerate 155 may be optimized when the angle of incidence θ is between 20° and 30° (e.g., 20°≤θ≤30°). For example, the size of the agglomerate 155 that is formed when the angle of incidence θ is between 20° and 30° may be larger because the magnitude of the acoustic streaming 162 may be maximized when the angle of incidence θ is between 20° and 30°. If the angle of incidence θ is too small (e.g., θ<15°), the incoming acoustic waves 160 may be nearly perpendicular to the surface of the suspension 150 within the well 115. This may give rise to sufficient acoustic pressure against the surface of the suspension 150 to cause the suspension 150 to atomize. When the angle of incidence θ is too large (e.g., θ>35°), the acoustic waves 160 may merely graze and/or even bypass the well 115 such that the resulting acoustic streaming 162 may be too weak to generate the vortex 164.

Figure 3A:
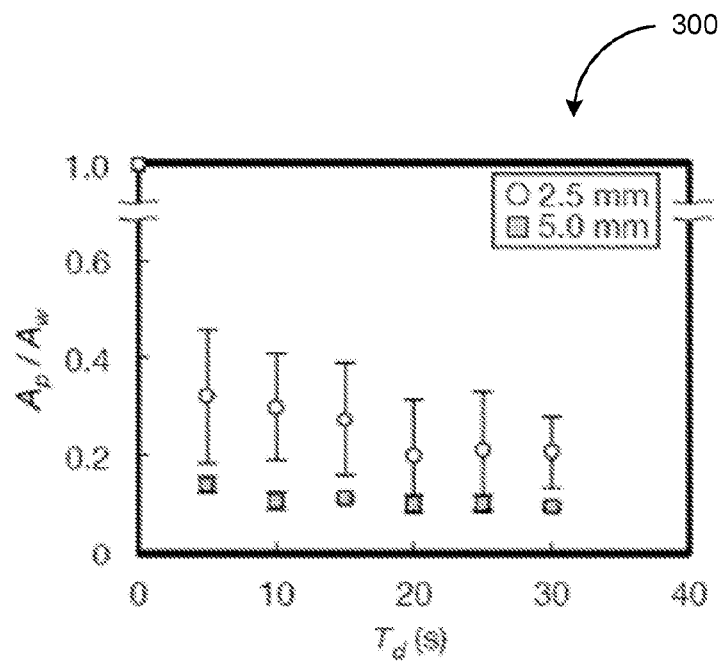
FIG. 3A depicts a graph illustrating agglomerate formation at different radial locations, in accordance to some example embodiments.
Figure 3B:
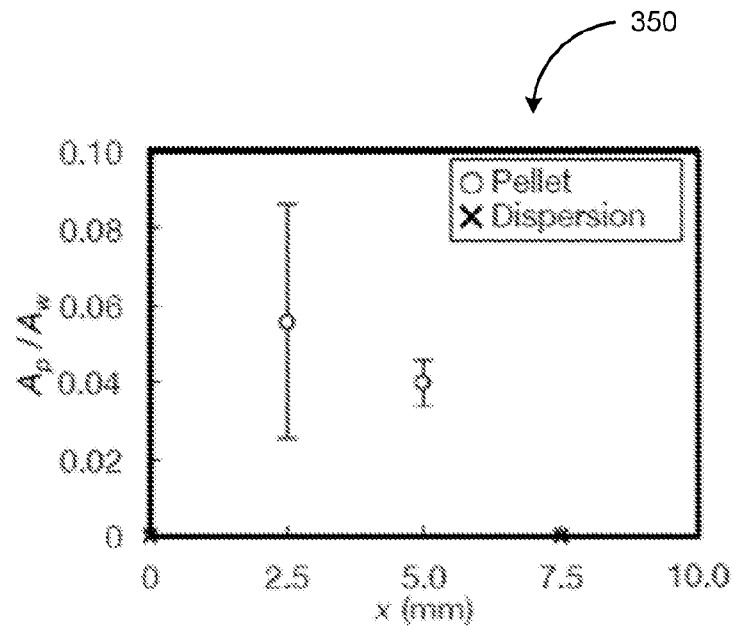
FIG. 3B depicts a graph illustrating agglomerate formation at different radial locations, in accordance to some example embodiments.
Figure 3C:
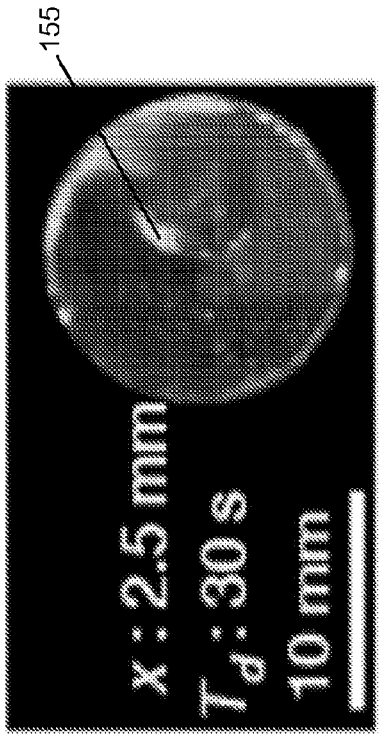
FIG. 3C depicts an image of an agglomerate formed with a 0 millimeter radial location, in accordance with some example embodiments.

FIGS. 3A-C depicts a relationship between the radial location x and the formation of the agglomerate 155, in accordance with some example embodiments. As noted, the radial location x may correspond to a distance between the acoustic streaming 162 in the suspension 150 and a center of the well 115. Referring to FIGS. 1A-C and 3A-F, the formation of the agglomerate 155 may be affected by varying the radial location x. As shown in FIGS. 3A-F, the formation of agglomerate 155 may vary at different radial locations x including, for example, 0 millimeter, 2 millimeters, 5.0 millimeters, and 7.5 millimeters, while the other parameters are held constant. For example, the angle of incidence θ may be fixed at 20°, the input power E may be fixed at 3.0 watts, the duty ratio D may be fixed at 100%, the total exposure time $T_d$ may be fixed at 30 seconds, and the concentration $N_p$ may be fixed at $1.0 \times 10^4$ particles per milliliter.

Figure 3D:
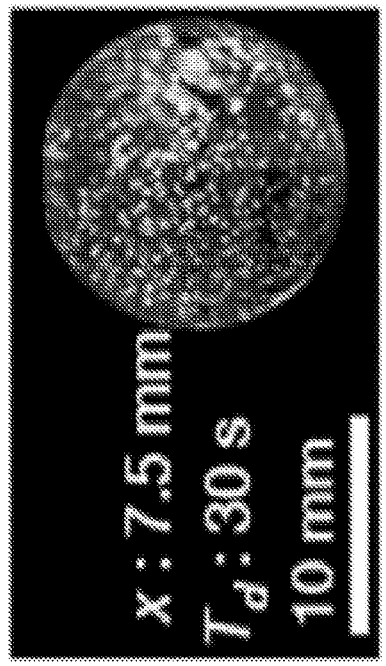
FIG. 3D depicts an image of an agglomerate formed with a 2.5 millimeter, in accordance with some example embodiments.
Figure 3E:
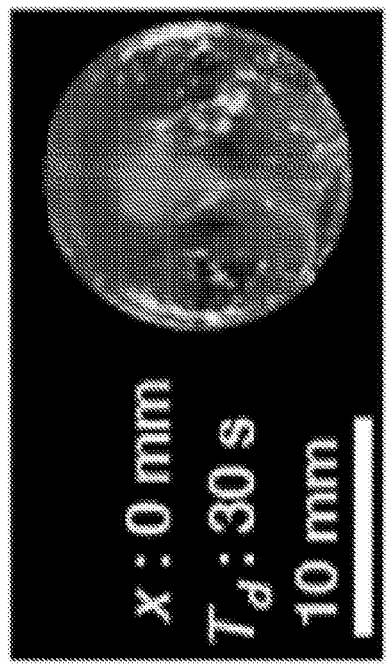
FIG. 3E depicts an image of an agglomerate formed with a 5.0 millimeter radial location, in accordance with some example embodiments.
Figure 3F:
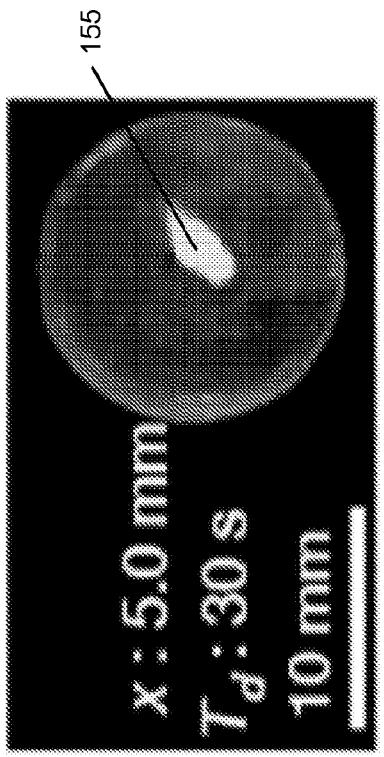
FIG. 3F depicts an image of an agglomerate formed with a 7.5 millimeter radial location, in accordance with some example embodiments.

To further illustrate, FIGS. 3A-B depict graphs illustrating the formation of the agglomerate 155 at different radial locations x, in accordance with some example embodiments. Referring to FIGS. 3A-B, the formation of the agglomerate 155 may be quantified based on a ratio $$\frac{A_p}{A_w},$$

wherein $A_p$ may correspond to a cross-sectional area occupied by the agglomerate 155 and $A_w$ may correspond to a cross-sectional area of the well 115. FIG. 3A depicts a graph 300 illustrating a change in the ratio $$\frac{A_p}{A_w}$$

at different radial locations x (e.g., 0 millimeter, 2.5 millimeters, 5.0 millimeters, and 7.5 millimeters) over the duration of the total exposure time $T_d$. Meanwhile, FIG. 3B depicts a graph 350 illustrating the relationship between the ratio $$\frac{A_p}{A_w}$$

and the radial location x. FIGS. 3C-F depict images of the agglomerate 155 formed at different radial locations x including, for example, 0 millimeter, 2.5 millimeters, 5.0 millimeters, and 7.5 millimeters. For example, FIG. 3C depicts an image of the agglomerate 155 that is formed when the radial location x is 0 millimeter, FIG. 3D depicts an image of the agglomerate 155 that is formed when the radial location x is 2.5 millimeters, FIG. 3E depicts an image of the agglomerate 155 that is formed when the radial location x is 5.0 millimeters, and FIG. 3F depicts an image of the agglomerate 155 that is formed when the radial location x is 7.5 millimeters.

As shown in FIGS. 3A-F, the formation of the agglomerate 155 may be optimized when the radial location x is between ½ and ¾ of the distance between a center of the well 115 and an edge of the well 115, which may correspond to being between 2.5 millimeters and 5.0 millimeters (e.g., 2.5 millimeters≤x≤5.0 millimeters). Notably, the particles forming the agglomerate 155 may be bound more loosely when the radial location x is 2.5 millimeters whereas the particles forming the agglomerate 155 may be bound more tightly when the radial location x is 5.0 millimeters. For instance, the agglomerate 155 shown in FIG. 3E may be better defined than the agglomerate 155 shown in FIG. 3D, indicating an increase in the stability of the agglomerate 155 when the acoustic streaming 162 is located farther away from the center of the well 115 then when the acoustic streaming 162 is located closer towards the center of the well 115. It should be appreciated acoustic streaming near the center of the well 115 may induce an upwelling of the suspension 150 that tends to destabilize the agglomerated 155 and cause the formation of the less defined agglomerate 155 shown in FIG. 3D.

FIGS. 4A-E depicts a relationship between the duty ratio D, the length of the burst period $T_b$, the input power E, and the formation of the agglomerate 155, in accordance with some example embodiments. As used herein, the duty ratio D may correspond to a proportion (e.g., percentage) of total elapsed time during which the acoustic wave device 110 may be generating the acoustic waves 160 and subjecting the suspension 150 to the acoustic streaming 162. For instance, when the duty ratio D is 75%, the acoustic wave device 110 may be generating the acoustic waves 160 and subjecting the suspension 150 to the acoustic streaming 162 during 75% of the total elapsed time. Alternatively and/or additionally, the acoustic wave device 110 may be generating the acoustic waves 160 continuously and constantly subjecting the suspension 150 to the acoustic streaming 162, when the duty ration D is 100%.

As noted, the acoustic waves 160 may be burst waves generated using pulse width modulation. Burst waves may reduce power and the concomitant risk of overheating the suspension 150. In some example embodiments, the length of the burst period $T_b$ may correspond to a duration of each burst of the acoustic waves 160. The length of the burst period $T_b$ may determine whether the acoustic waves 160 generated by the acoustic device 110 is sufficient to induce the acoustic streaming 162 within the well 115 and cause the formation of the agglomerate 155.

Referring to FIGS. 1A-C and 4A-E, the formation of agglomerate 155 may vary at different duty ratios D including, for example, 25%, 50%, and 75%. The formation of the agglomerate 155 may also vary at different burst periods $T_b$ including, for example, 2 milliseconds, 20 milliseconds, and 200 milliseconds. Alternatively and/or additionally, the formation of the agglomerate 1155 may also vary at different input power E including, for example, 0.75 watts and 1.5 watts. It should be appreciated that other parameters that may affect the formation of the agglomerate 155 may be held constant. For example, the angle of incidence θ may be fixed at 20°, the radial location x may be fixed at 5.0 millimeters, and the concentration $N_p$ may be fixed to $1.0 \times 10^4$ particles per milliliter.

Figure 4A:
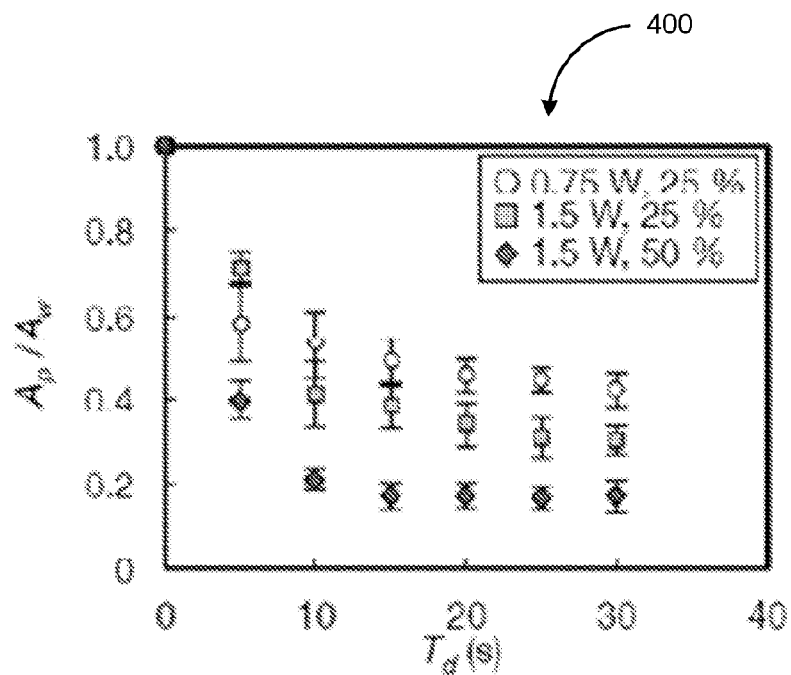
FIG. 4A depicts a graph illustrating agglomerate formation at different duty ratios and input powers, in accordance to some example embodiments.
Figure 4B:
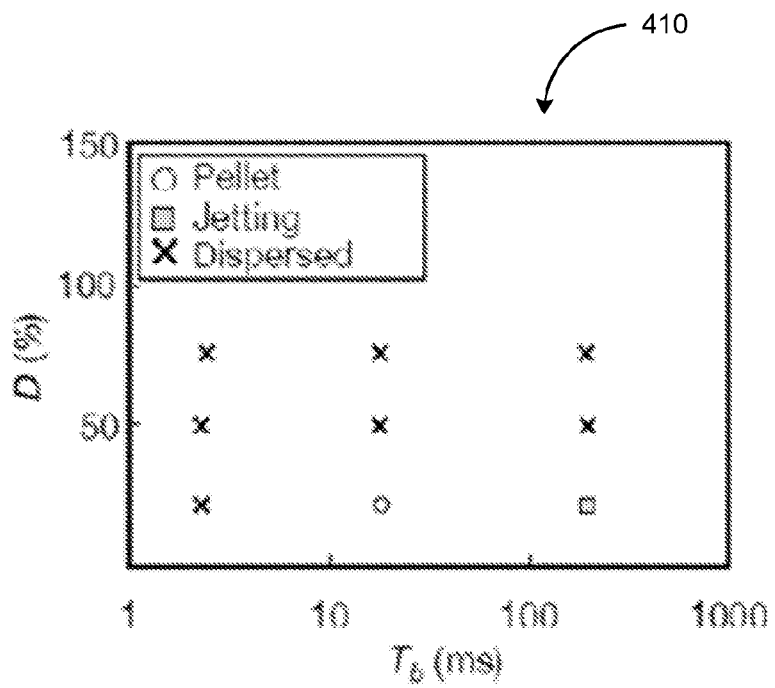
FIG. 4B depicts a graph illustrating agglomerate formation at a fixed input power with different duty ratios and lengths of burst periods, in accordance to some example embodiments.
Figure 4C:
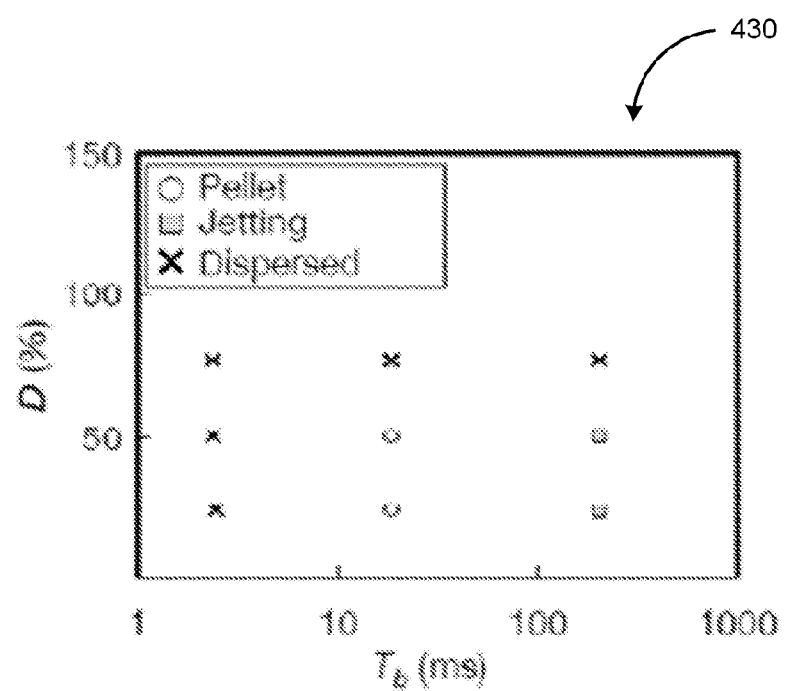
FIG. 4C depicts a graph illustrating agglomerate formation at a fixed input power with different duty ratios and lengths of burst period, in accordance with some example embodiments.

To further illustrate, FIGS. 4A-C depict graphs illustrating the formation of the agglomerate 155 at different duty ratios D, lengths of burst period $T_b$, and/or input powers E, in accordance with some example embodiments. FIG. 4A depicts a graph 400 illustrating the formation of the agglomerate 155 over the duration of the total exposure time $T_d$ when the suspension 150 is subject to different combinations of duty ratios D and input powers E. For example, the formation of the agglomerate 155 may be quantified based on a ratio $$\frac{A_p}{A_w},$$

wherein $A_p$ may correspond to a cross-sectional area occupied by the agglomerate 155 and $A_w$ may correspond to a cross-sectional area of the well 115. The graph 400 plots the different values of the ratio $$\frac{A_p}{A_w}$$

that are observed when the input power E is 0.75 watts and the duty ratio D is 25%, when the input power E is 1.5 watts and the duty ratio D is 25%, and when the input power E is 1.5 watts and the duty ratio D is 50%.

Figure 4D:
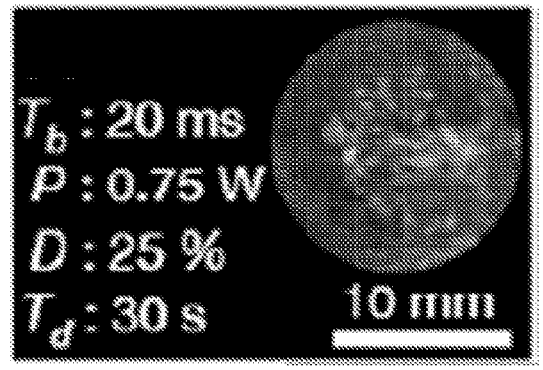
FIG. 4D depicts an image of an agglomerate formed with an input power of 0.75 watts and a duty ratio of 25%, in accordance with some example embodiments.
Figure 4E:
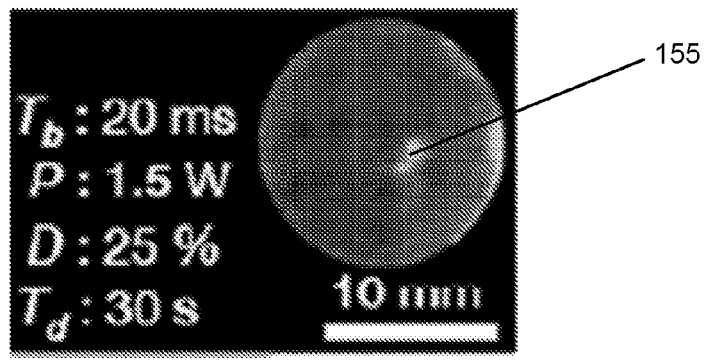
FIG. 4E depicts an image of an agglomerate formed with an input power of 1.5 watts and a duty ratio of 25%, in accordance with some example embodiments.
Figure 4F:
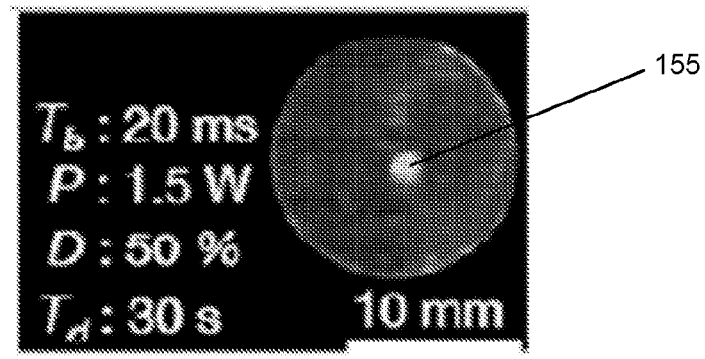
FIG. 4F depicts an image of an agglomerate formed with an input power of 1.5 watts and a duty ratio of 50%, in accordance with some example embodiments.

FIG. 4B depicts a graph 410 illustrating the formation of the agglomerate 155 at various combinations of duty ratios D and lengths of burst period $T_b$ while the input power E is held constant at 0.75 watts. Meanwhile, FIG. 4C depicts a graph 420 illustrating the formation of the agglomerate 155 at various combinations of duty ratios D and lengths of burst period $T_b$ while the input power E is held constant at 1.5 watts. FIGS. 4D-F depicts images of the agglomerate 155 formed at different combinations of input power E and duty ratios D. For example, FIG. 4D depicts the agglomerate 155 that is formed when the input power E is 0.75 watts and the duty ratio D is 25%, FIG. 4E depicts the agglomerate 155 that is formed when the input power E is 1.5 watts and the duty ratio D is 25%, and FIG. 4F depicts the agglomerate 155 that is formed when the input power E is 1.5 watts and the duty ratio D is 50%.

Referring to FIGS. 4B-F, the agglomerate 155 may form at select combinations of the duty ratio D, the length of the burst period $T_b$, and the input power E. For instance, when the input power E is 0.75 watts, a duty ratio D of 25% and a burst period $T_b$ of 20 milliseconds may be required to form the agglomerate 155. Alternatively and/or additionally, when the input power E is 1.5 watts, a burst period $T_b$ of 20 milliseconds and a duty ratio D of either 25% or 50% may be required to form the agglomerate 155. Other combinations of duty ratios D, burst periods $T_b$, and input powers E may not produce the agglomerate 155. For instance, a too short burst period $T_b$ (e.g., 2 milliseconds) may not induce the acoustic streaming 162, which may be necessary to form the agglomerate 155. A lengthy burst period $T_b$ (e.g., 200 milliseconds) may also prevent the formation of the agglomerate 155 by causing an excessive dispersion of the solid particles within the suspension 150 and/or even portions of the suspension 155 to be jetted from the well 115.

FIGS. 5A-E depicts the relationship between the length of the burst period $T_b$ and the formation of the agglomerate 155, in accordance with some example embodiments. As noted, the formation of the agglomerate 155 may be affected by varying the length of the burst period $T_b$. Here, FIGS. 5A-E illustrates the formation of the agglomerate 155 at different burst periods $T_b$ including, for example, 12 milliseconds, 16 milliseconds, 20 milliseconds, and 24 milliseconds while other parameters are held constant. For example, the angle of incidence θ may be fixed at 20°, the radial location x may be fixed at 5.0 millimeters, the input power E may be fixed at 1.5 watts, the duty ratio D may be fixed at 50%, the total exposure time $T_d$ may be fixed to 30 seconds, and the concentration $N_p$ may be fixed to $1.0 \times 10^4$ particles per milliliter.

Figure 5A:
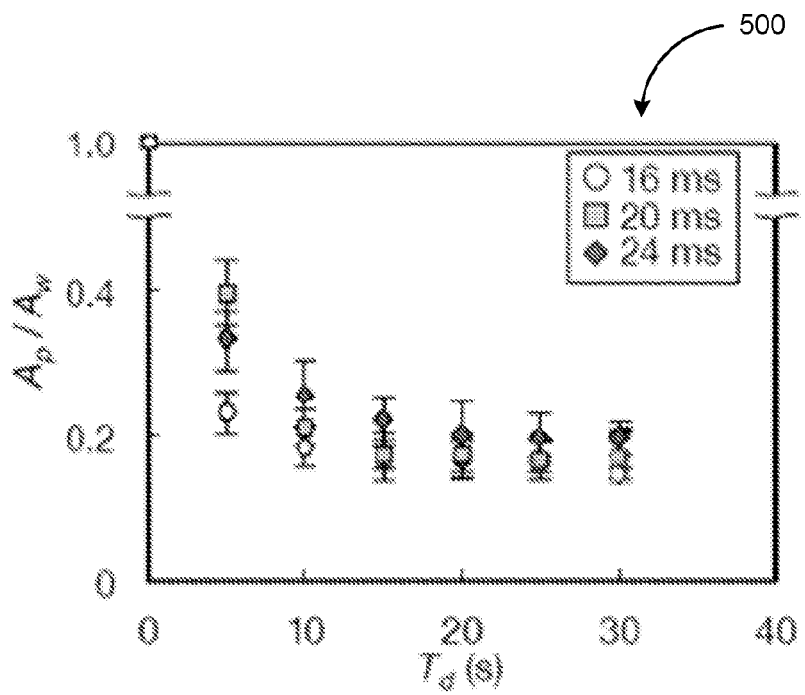
FIG. 5A depicts a graph illustrating agglomerate formation at different length burst periods, in accordance to some example embodiments.
Figure 5B:
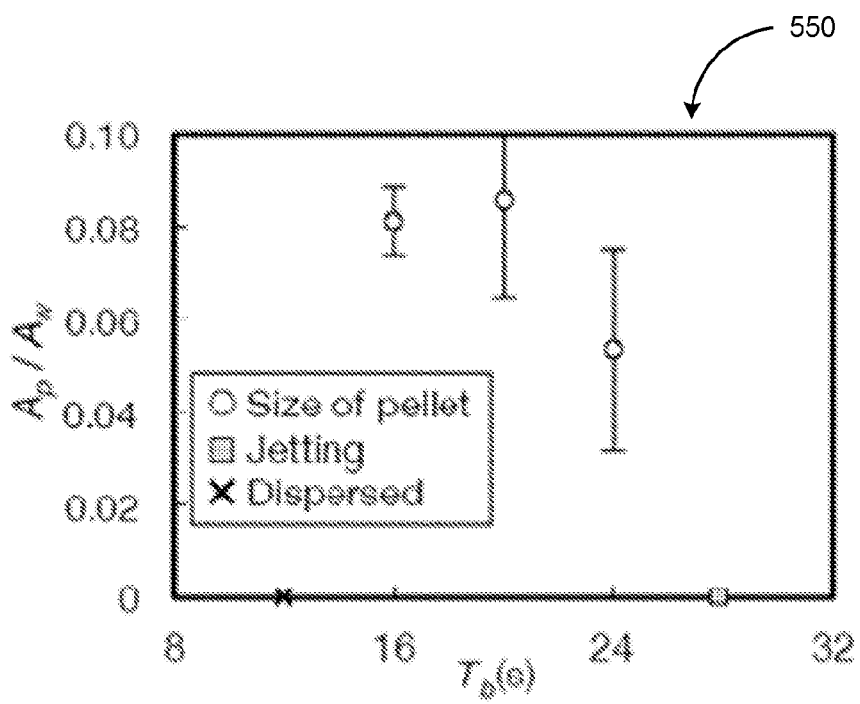
FIG. 5B depicts a graph illustrating agglomerate formation at different lengths burst periods, in accordance to some example embodiments.
Figure 5C:
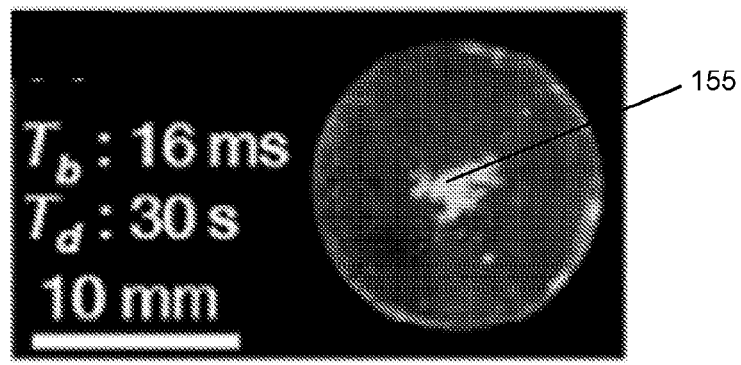
FIG. 5C depicts an image of an agglomerate formed with 16-millisecond burst period, in accordance with some example embodiments.
Figure 5D:
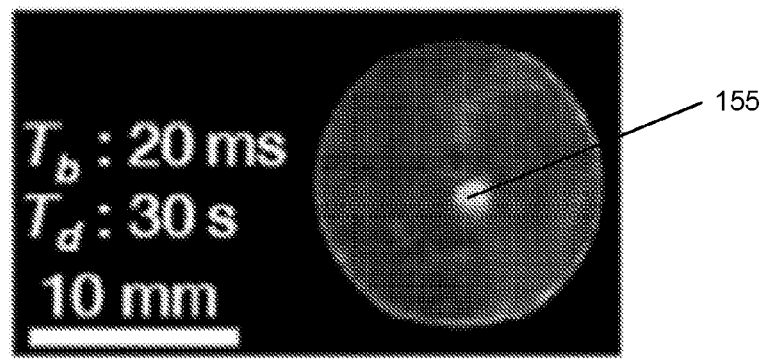
FIG. 5D depicts an image of an agglomerate formed with a 20-millisecond burst period, in accordance with some example embodiments.
Figure 5E:
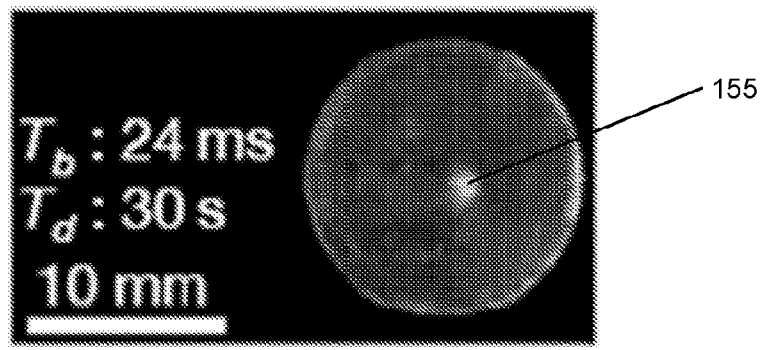
FIG. 5E depicts an image of an agglomerate formed with a 24-millisecond burst period, in accordance with some example embodiments.

To further illustrate, FIGS. 5A-B depict graphs illustrating the formation of the agglomerate 155 with different burst periods $T_b$, in accordance with some example embodiments. Referring to FIGS. 5A-B, the formation of the agglomerate 155 may be quantified based on a ratio $$\frac{A_p}{A_w},$$

wherein $A_p$ may correspond to a cross-sectional area occupied by the agglomerate 155 and $A_w$ may correspond to a cross-sectional area of the well 115. FIG. 5A depicts a graph 500 illustrating a change in the ratio $$\frac{A_p}{A_w}$$

at different length burst periods $T_b$ (e.g., 16 milliseconds, 20 milliseconds, and 24 milliseconds) over the duration of the total exposure time $T_d$. Meanwhile, FIG. 2B depicts a graph 550 illustrating the relationship between the ratio ratio $$\frac{A_p}{A_w}$$

and the length of the burst period $T_b$. FIGS. 5C-E depict images of the agglomerate 155 formed at different length burst periods $T_b$ including, for example, 16 milliseconds, 20 milliseconds, and 24 milliseconds. For example, FIG. 5C depicts an image of the agglomerate 155 formed with a 16-millisecond long burst period $T_b$, FIG. 5D depicts an image of the agglomerate 155 formed with a 20-millisecond long burst period $T_b$, and FIG. 5E depicts an image of the agglomerate 155 formed with a 24-millisecond long burst period $T_b$.

As shown in FIGS. 5A-E, the formation of the agglomerate 155 may be optimized when the length of the burst period $T_b$ is 16 milliseconds. That is, subjecting the suspension 150 to 16-millisecond long bursts of the acoustic waves 160 may yield a larger, more cohesive agglomerate 155. By contrast, the agglomerate 155 may fail to form when the length of the burst period $T_b$ is too short (e.g., 12 milliseconds) because a too short burst period $T_b$ may not induce the acoustic streaming 162 required to form the agglomerate 155. The agglomerate 155 may also fail to form when the length of the burst period $T_b$ is too long (e.g., 24 milliseconds) because a too long burst period $T_b$ may over agitate the suspension 150, thereby causing an excessive dispersion of the solid particles within the suspension 150 and/or even portions of the suspension 155 to be jetted from the well 115.

FIG. 6A-G depicts the relationship between the concentration $N_p$ and the formation of the agglomerate 155, in accordance with some example embodiments. As used herein, the concentration $N_p$ may correspond to a proportion of solid particles (e.g., cells) in the suspension 150. Referring to FIGS. 1A-C and 6A-E, the formation of agglomerate 155 may vary at different concentration $N_p$ including, for example, $1.0 \times 10^3$ particles per milliliter, $5.0 \times 10^3$ particles per milliliter, $1.0 \times 10^4$ particles per milliliter, $5.0 \times 10^4$ particles per milliliter, and $1.0 \times 10^1$ particles per milliliter while the other parameters are held constant. For example, the radial location x may be fixed at 5.0 millimeters, the input power E may be fixed at 3.0 watts, the duty ratio D may be fixed at 50%, the total exposure time $T_d$ may be fixed to 30 seconds, and the length of the burst period $T_b$ may be fixed to 16 milliseconds.

Figure 6A:
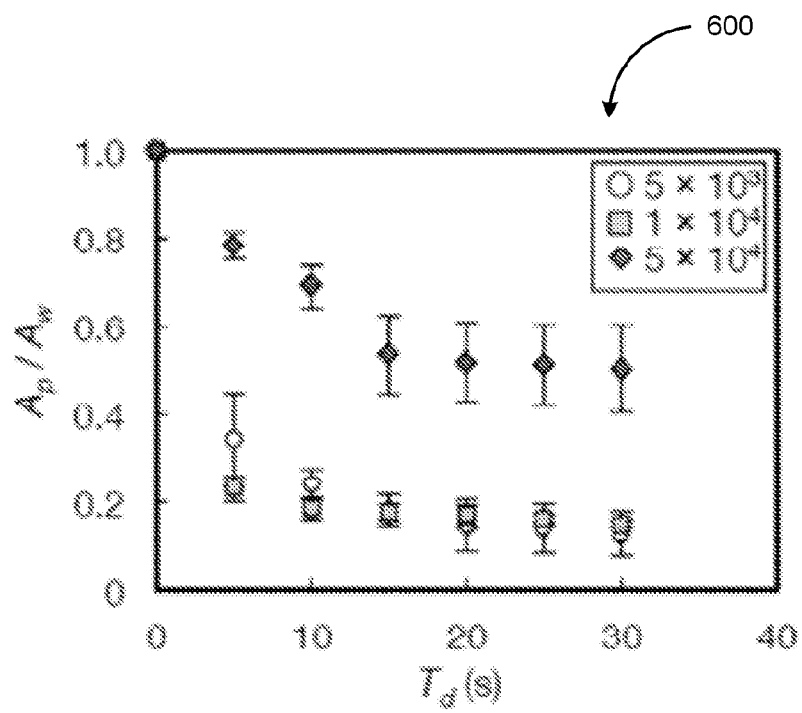
FIG. 6A depicts a graph illustrating agglomerate formation at different concentrations of solid particles, in accordance to some example embodiments.
Figure 6B:
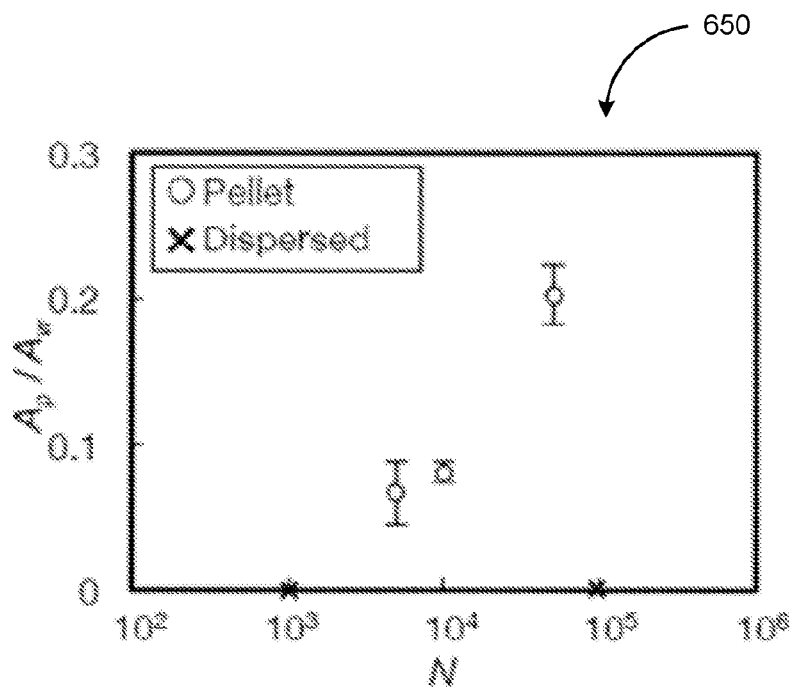
FIG. 6B depicts a graph illustrating agglomerate formation at different concentrations of solid particles, in accordance to some example embodiments.
Figure 6C:
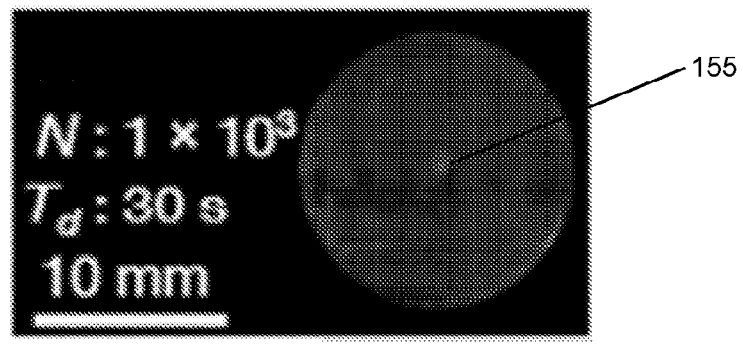
FIG. 6C depicts an image of an agglomerate formed at a concentration of $1.0 \times 10^3$ particles per milliliter, in accordance with some example embodiments.
Figure 6D:
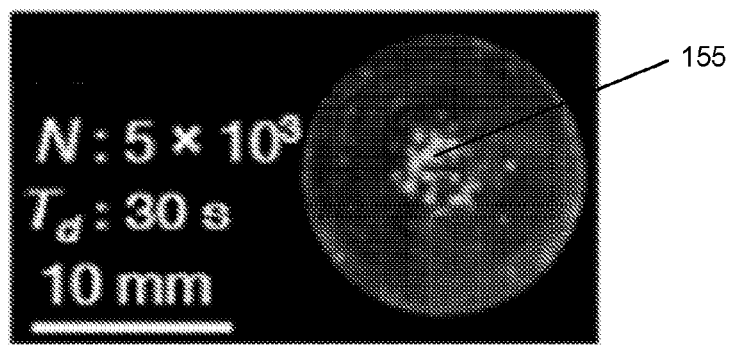
FIG. 6D depicts an image of an agglomerate formed at a concentration of $5.0 \times 10^3$ particles per milliliter, in accordance with some example embodiments.
Figure 6E:
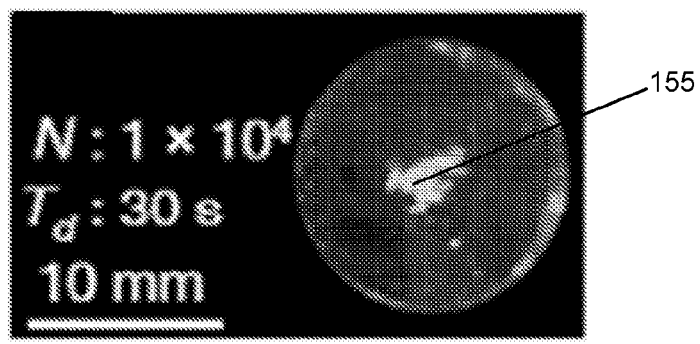
FIG. 6E depicts an image of an agglomerate formed at a concentration of $1.0 \times 10^4$ particles per milliliter, in accordance with some example embodiments.
Figure 6F:
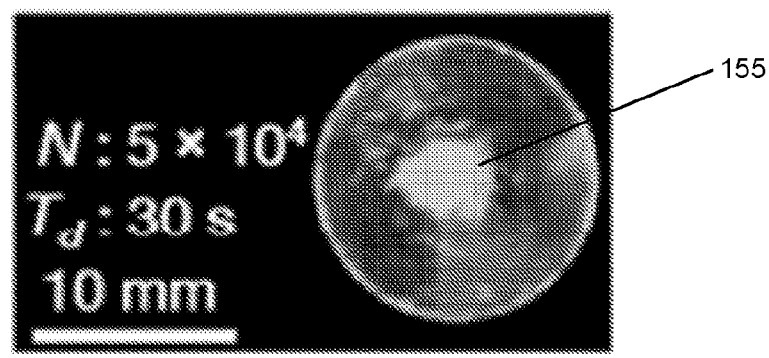
FIG. 6F depicts an image of an agglomerate formed at a concentration of $5.0 \times 10^4$ particles per milliliter, in accordance with some example embodiments.
Figure 6G:
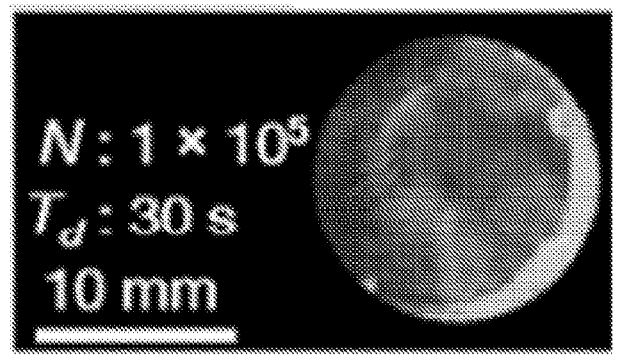
FIG. 6G depicts an image of an agglomerate formed at a concentration of $1.0 \times 10^5$ particles per milliliter, in accordance with some example embodiments.

To further illustrate, FIGS. 6A-B depict graphs illustrating the formation of the agglomerate 155 at different concentrations $N_p$, in accordance with some example embodiments. Referring to FIGS. 6A-B, the formation of the agglomerate 155 may be quantified based on a ratio $$\frac{A_p}{A_w},$$

wherein $A_p$ may correspond to a cross-sectional area occupied by the agglomerate 155 and $A_w$ may correspond to a cross-sectional area of the well 115. FIG. 6A depicts a graph 600 illustrating a change in the ratio $$\frac{A_p}{A_w}$$

at different concentrations $N_p$ (e.g., $5.0 \times 10^3$ particles per milliliter, $1.0 \times 10^4$ particles per milliliter, and $5.0 \times 10^4$ particles per milliliter) over the duration of the total exposure time $T_d$. Meanwhile, FIG. 6B depicts a graph 650 illustrating the relationship between the ratio ratio $$\frac{A_p}{A_w}$$

and the concentration $N_p$. FIGS. 6C-G depict images of the agglomerate 155 formed at different concentration $N_p$ including, for example, $1.0 \times 10^3$ particles per milliliter, $5.0 \times 10^3$ particles per milliliter, $1.0 \times 10^4$ particles per milliliter, $5.0 \times 10^4$ particles per milliliter, and $1.0 \times 10^5$ particles per milliliter. For example, FIG. 6C depicts an image of the agglomerate 155 that is formed when the concentration $N_p$ is $1.0 \times 10^3$ particles per milliliter, FIG. 6D depicts an image of the agglomerate 155 that is formed when the concentration $N_p$ is $5.0 \times 10^3$ particles per milliliter, FIG. 6E depicts an image of the agglomerate 155 that is formed when the concentration $N_p$ is $1.0 \times 10^4$ particles per milliliter, FIG. 6F depicts an image of the agglomerate 155 that is formed when the concentration $N_p$ is $5.0 \times 10^4$ particles per milliliter, and FIG. 6G depicts an image of the agglomerate 155 that is formed when the concentration $N_p$ is $1.0 \times 10^5$ particles per milliliter.

As shown in FIGS. 6A-G, higher concentrations $N_p$ did not necessarily yield a larger and/or more cohesive agglomerate 155. For instance, as shown in FIG. 6G, a loosely bound agglomerate 155 may be formed when the concentration $N_p$ is high (e.g., $N_p = 1.0 \times 10^5$ particles per milliliter). Meanwhile, the formation of the agglomerate 155 may be optimized at intermediate concentrations $N_p$ including, for example, $5.0 \times 10^3$ particles per milliliter and $1.0 \times 10^4$ particles per milliliter. Notably, the agglomerate 155 that is formed when the concentration $N_p$ is $1.0 \times 10^4$ particles per milliliter may be the most cohesive and well-defined.

Figure 7A:
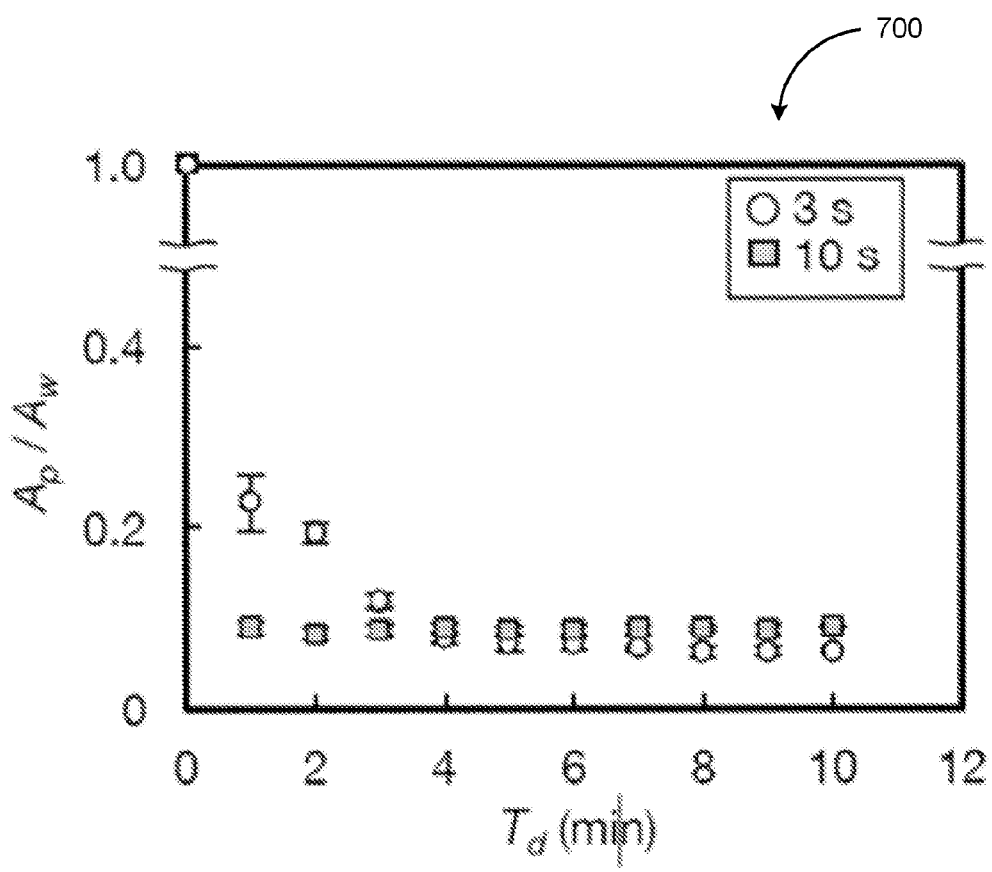
FIG. 7A depicts a graph illustrating agglomerate formation at different lengths exposure cycles, in accordance with some example embodiments.
Figure 7B:
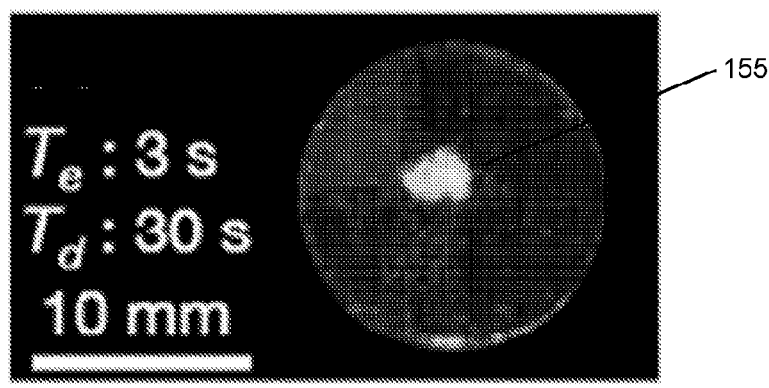
FIG. 7B depicts an image of an agglomerate formed with a 3 second per minute exposure cycle, in accordance with some example embodiments.
Figure 7C:
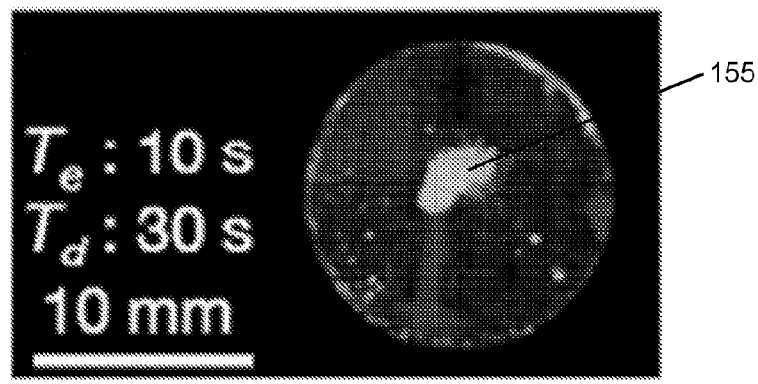
FIG. 7C depicts an image of an agglomerate formed with a 10 second per minute exposure cycle, in accordance with some example embodiments.

FIGS. 7A-C depicts a relationship between the length of the exposure cycles $T_i$ and the formation of the agglomerate 155, in accordance with some example embodiments. As noted, the suspension 150 may be subject to intermittent bursts of acoustic waves 160. Meanwhile, the acoustic waves 160 may induce the acoustic streaming 162 in the suspension 150. Accordingly, the length of the exposure cycle $T_i$ may correspond to the duration of the period of time during which the suspension 150 is exposed to the acoustic streaming 162.

Referring to FIGS. 1A-C and 7A-E, the formation of the agglomerate 155 may be affected by varying the length of the exposure cycles $T_i$, for example, between 3 seconds per minute and 10 seconds per minute, while the other parameters are held constant. For example, the angle of incidence θ may be fixed at 20°, the radial location x may be fixed at 5.0 millimeters, the input power E may be fixed at 3.0 watts, the duty ratio D may be fixed at 50%, the total exposure time $T_d$ may be fixed to 10 minutes, the length of the burst period $T_b$ may be fixed to 16 milliseconds, and the concentration $N_p$ may be fixed to $1.0 \times 10^4$ particles per milliliter.

To further illustrate, FIG. 7A depicts a graph 700 illustrating the formation of the agglomerate 155 with different lengths exposure cycles $T_i$, in accordance with some example embodiments. As shown in FIG. 7A, the formation of the agglomerate 155 may be quantified based on a ratio $$\frac{A_p}{A_w},$$

wherein $A_p$ may correspond to a cross-sectional area occupied by the agglomerate 155 and $A_w$ may correspond to a cross-sectional area of the well 115. The graph 700 plots the different values of the ratio $$\frac{A_p}{A_w}$$

that are observed over the course of the total exposure time $T_d$ when the suspension 150 is subject to different lengths exposure cycles $T_i$ including, for example, 3 seconds per minute and 10 seconds per minute. FIGS. 7B-C depicts images of the agglomerate 155 formed at different lengths exposure cycles $T_i$. For example, FIG. 7B depicts the agglomerate 155 that is formed when the suspension 150 is exposed to the acoustic streaming 162 for 3 seconds every minute while FIG. 7C depicts the agglomerate 150 that is formed when the suspension 150 is exposed to the acoustic streaming 162 for 10 seconds per minute. As shown in FIGS. 7A-C, the formation of the agglomerate 155 may be optimized when the suspension 150 is subject to shorter exposure cycles $T_i$ (e.g., $T_i = 3$ seconds per minute).

Figure 8:
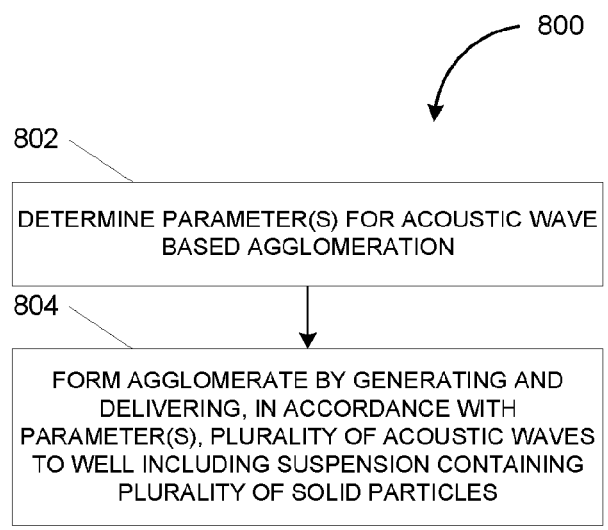
FIG. 8 depicts a flowchart illustrating a process for acoustic wave based agglomeration, in accordance with some example embodiments.

FIG. 8 depicts a flowchart illustrating a process 800 for acoustic wave based agglomeration, in accordance with some example embodiments. Referring to FIGS. 1-8, the process 700 may be performed by the apparatus 100.

At 802, one or more parameters for acoustic wave based agglomeration may be determined. In some example embodiments, the apparatus 100 may be configured to generate the acoustic waves 160, which may induce the acoustic streaming 162 within the suspension 150 and cause the formation of the agglomerate 155. As noted, the agglomerate 155 may be a three-dimensional formation of living cells. The parameters for generating the agglomerate 155 may include the angle of incidence θ of the acoustic waves 160, the radial location x of the acoustic streaming 162, the input power E applied to the acoustic wave device 110, the duty ratio D of the acoustic waves 160, the total exposure time $T_d$ to the acoustic waves 160, the length of a burst period $T_b$ of the acoustic waves 160, and/or the concentration $N_p$ of the solid particles within the suspension 150.

According to some example embodiments, the formation of the agglomerate 155 may be optimized when the angle of incident θ is between 5° and 55° from a bottom of the well 115, the radial location x is ½ to ¾ of the distance between a center of the well 115 and an edge of the well 115, the input power E is intermittent at 50 milliwatts to 5.0 watts, the duty ratio D is between 10% and 50%, the length of the burst period $T_b$ is between 1 second to 100 seconds, the length of the burst cycle $T_i$ is between 0.1 seconds per minute to 15 seconds per minute, and the total exposure time $T_d$ is 1 cycle to 1000 cycles.

At 804, the apparatus 100 may form the agglomerate 155 by at least generating and delivering, in accordance with the one or more parameters, a plurality of acoustic waves to a well including a suspension containing a plurality of solid particles. For example, the acoustic wave device 110 may generate the plurality of acoustic waves 160, which may be delivered to the well 115 via the couplant material 140. The acoustic waves 160 may induce, within the suspension 150 held in the well 115, the acoustic streaming 162. The acoustic streaming 162 may generate the vortex 164, which may a shear-induced migration of the solid particles in the suspension 150. The agglomerate 155 may be formed when the vortex 164 cause at least a portion of the solid particles to concentrate toward a center of the well 115.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus, comprising:
a well including a suspension comprising a plurality of particles; and
an acoustic wave device configured to generate a plurality of acoustic waves, wherein the plurality of acoustic waves induce acoustic streaming and formation of a vortex within the suspension contained by the well, wherein the acoustic streaming including the vortex agitates the suspension to cause formation of an agglomerate within the well, wherein the agglomerate comprises at least a portion of the plurality of particles,
wherein an orientation of the acoustic wave device is configured such that the plurality of acoustic waves enters a bottom portion of the well, wherein the well comprises a top portion through which the suspension is inserted into the well and the bottom portion contains the suspension along with a side portion of the well,
wherein the acoustic wave device comprises a piezoelectric material configured to convert electric energy into the plurality of acoustic waves, wherein the acoustic wave device comprising the piezoelectric material is oriented via one or more ramps to control the angle of incidence of the plurality of acoustic waves entering the bottom portion of the well and to control a distance between the acoustic streaming in the suspension and a center of the well, wherein the acoustic wave device comprising the piezoelectric material is coupled to the well via a couplant material, wherein the well is at least partially submerged in the couplant material, and
wherein the orientation of the acoustic wave device is configured such that the plurality of acoustic waves enters, based on the orientation provided by the one or more ramps, via the bottom portion of the well.

2. The apparatus of claim 1, wherein the agglomerate comprises a 3-dimensional formation comprising at least the portion of the plurality of particles.

3. The apparatus of claim 1, wherein the plurality of particles comprise cells.

4. The apparatus of claim 1, wherein the suspension comprises a mixture of the plurality of particles and one or more fluids.

5. The apparatus of claim 1, wherein the piezoelectric material comprises a monocrystalline and/or a polycrystalline.

6. The apparatus of claim 1, wherein 50 milliwatts to 5.0 watts of electric power is applied to the piezoelectric material in order to cause the acoustic wave device to generate the plurality of acoustic waves.

7. The apparatus of claim 1, wherein the acoustic wave device is configured to generate the plurality of acoustic waves in one or more intermittent bursts.

8. The apparatus of claim 7, wherein a length of the one or more intermittent bursts of acoustic waves is between 1 second and 100 seconds.

9. The apparatus of claim 7, wherein each of the one or more intermittent bursts of acoustic waves triggers a corresponding cycle of the acoustic streaming.

10. The apparatus of claim 9, wherein the acoustic wave device is configured to expose the suspension to between 1 cycle to 1000 cycles of the acoustic streaming, and wherein each cycle of the acoustic streaming is between 0.1 seconds per minute to 15 seconds per minute.

11. The apparatus of claim 1, wherein the acoustic wave device is configured to operate in accordance with a duty ratio, and wherein the duty ratio corresponds to a proportion of total elapsed time during which the acoustic wave device is generating the plurality of acoustic waves.

12. The apparatus of claim 11, wherein the duty ratio is between 10% and 50%.

13. The apparatus of claim 1, wherein the apparatus further comprises the couplant material configured to transmit the plurality of acoustic waves from the acoustic wave device to the well.

14. The apparatus of claim 1, wherein the acoustic wave device is oriented such that the plurality of acoustic waves enters the bottom portion of the well at between an 5° angle of incidence and an 55° angle of incidence.

15. The apparatus of claim 1, wherein the acoustic wave device is oriented such that the acoustic streaming is induced at between to of a distance between ½ to ¾ of a distance between a center of the well and an edge of the well.

* * * * *

UNITED STATES PATENT AND TRADEMARK OFFICE
CERTIFICATE OF CORRECTION

| | |
|---|---|
| PATENT NO. | : 11,560,557 B2 |
| APPLICATION NO. | : 16/461753 |
| DATED | : January 24, 2023 |
| INVENTOR(S) | : James Friend et al. |

It is certified that error appears in the above-identified patent and that said Letters Patent is hereby corrected as shown below:

On the Title Page

In the Related U.S. Application Data:
At Page 2, in item (60), first line, delete "Provisional application No. 62/242,098" and insert
--Provisional Application No. 62/424,098--.

Signed and Sealed this
Twenty-first Day of March, 2023

Katherine Kelly Vidal
*Director of the United States Patent and Trademark Office*